United States Patent [19]

Woolard

[11] Patent Number: 4,867,780
[45] Date of Patent: Sep. 19, 1989

[54] 2-(ACYLIMINO)THIAZOLIDINE HERBICIDES

[75] Inventor: Frank X. Woolard, Richmond, Calif.
[73] Assignee: ICI Americas, Inc., Wilmington, Del.
[21] Appl. No.: 214,348
[22] Filed: Jul. 1, 1988
[51] Int. Cl.$^4$ .................. C07D 277/18; A01N 47/18; A01N 47/36; A01N 43/78
[52] U.S. Cl. ........................................ 71/90; 548/195; 548/196
[58] Field of Search ..................... 548/195, 196; 71/90

[56] References Cited

U.S. PATENT DOCUMENTS 4,181,001  1/1980  Rooney ............................... 548/195

FOREIGN PATENT DOCUMENTS 41471  2/1988  Japan ................................... 548/233

Primary Examiner—Robert Gerstl
Attorney, Agent, or Firm—Joel G. Ackerman

[57] ABSTRACT

Herbicidal compounds have the formula

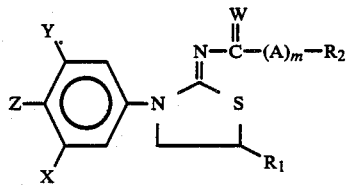

in which W is oxygen or sulfur; X is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, difluoromethoxy, trifluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$–$C_4$ alkyloximinomethyl, benzyloximinomethyl, 1-($C_1$–$C_4$ alkyl)-oximinoethyl and 1-benzyloximinoethyl; Y is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, trifluoromethoxy, tetrafluoroethoxy, methylsulfonyl and trifluoromethylsulfonyl; Z is hydrogen or fluoro if Y is hydrogen, or hydrogen if Y is other than hydrogen; $R_1$ is hydrogen, methyl, ethyl or chloromethyl; A is oxygen, sulfur,

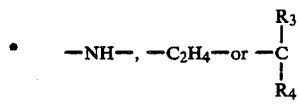

in which $R_3$ and $R_4$ are independently hydrogen, methyl or methoxy; and $R_2$ is alkyl; carboalkoxy; carboalkoxyalkylene; haloalkyl; alkoxy; optionally methylsubstituted cycloalkyl; phenyl; substituted phenyl; phenoxy; halophenoxy; styryl; p-chlorophenylsulfonyl; haloalkylcarbonyl; napthyl; halonapthyl; benzoyl; halo-substituted benzyl; polycyclic aliphatic; mono- or dialkylamino; benzoyl; or a 5- to 6-member heterocyclic ring containing 1–2 oxygen or sulfur atoms, optionally substituted; and m is 0 or 1.

35 Claims, No Drawings

2-(ACYLIMINO)THIAZOLIDINE HERBICIDES

BACKGROUND OF THE INVENTION

The present invention relates to certain 2-(acylimino)thiazolidine herbicidal compounds, compositions, and methods of use.

There are a number of different types pof herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil. Some herbicides are effective both as pre- and post-emergence herbicides. The iminothiazolidines of this invention fall into that category.

DESCRIPTION OF THE INVENTION

The compounds of this invention have the formula:

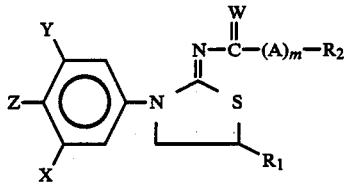

in which
W is oxygen or sulfur;
X is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, difluoromethoxy, trifluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$–$C_4$ alkyloximinomethyl, benzyloximinomethyl, 1-($C_1$–$C_4$ alkyl)oximinoethyl and 1-benzyloximinoethyl;
Y is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, trifluoromethoxy, tetrafluoroethoxy, methylsulfonyl and trifluoromethylsulfonyl;
Z is hydrogen or fluoro if Y is hydrogen, or hydrogen if Y is other than hydrogen;
$R_1$ is hydrogen, methyl, ethyl or chloromethyl;
A is oxygen, sulfur,

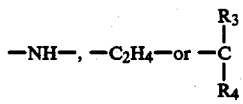

in which $R_3$ and $R_4$ are independently hydrogen, methyl or methoxy; and
$R_2$ is $C_1$–$C_6$ alkyl; carbo($C_1$–$C_6$)-alkoxy; carbo($C_1$–$C_6$)alkoxy($C_1$–$C_2$ alkylene); $C_1$–$C_4$ haloalkyl if m is 1; $C_2$–$C_4$ haloalkyl if m is 0; $C_1$–$C_5$ alkoxy; $C_3$–$C_6$ cycloalkyl optionally substituted by up to 2 methyl groups; $C_2$–$C_6$ alkenyl; phenyl; substituted phenyl in which the substituents are $C_1$–$C_4$ alkyl, halogen, trifluoromethyl, nitro, $C_1$–$C_4$ alkoxy, $C_1$–$C_4$ alkylthio, or cyano; phenoxy; halosubstituted phenoxy; styryl; p-chlorophenylsulfonyl; $C_2$–$C_4$ haloalkylcarbonyl; naphthyl; benzoyl; halosubstituted benzoyl; a polycyclic aliphatic group having from 6 to 12 carbon atoms; amino; mono- or di-($C_1$–$C_4$)alkylamino; $C_3$–$C_8$ alkynyl; cyano; benzyl; or a saturated or unsaturated heterocyclic ring containing from 5 to 6 atoms including from 1 to 2 hetero atoms selected from oxygen and sulfur, optionally substituted by from 1 to 3 methyl groups and/or from 1 to 2 oxo groups; and
m is 0 or 1;
provided that:
(a) when A is —NH— and $R_2$ is phenyl or substituted phenyl, then W is oxygen; and
(b) when A is oxygen and $R_2$ is substituted phenyl, the substituents on the phenyl ring are not meta-directing electron-withdrawing groups; and
(c) when $R_2$ is cyano or $C_3$–$C_8$ alkynyl and m is 1, then A is —$CH_2$—.

The term "alkyl" refers to straight and branched chain acyclic hydrocarbyl moieties having the number of carbon atoms associated with that term whenever used (i.e., by itself or as part of the definition of another moiety, e.g., "haloalkyl", "alkylthio," etc.). Examples of alkyl groups include methyl, ethyl, n-propyl, isopropyl, n-butyl, isobutyl, sec-butyl, tert-butyl, and the various pentyl, hexyl, etc. moieties. The term "iso-$C_5H_{11}$" (isoamyl or isopentyl) designates the group 3-methylbutyl. The term "sec-$C_5H_{11}$" designates the 2-pentyl group.

The term "carboalkoxy" refers to moieties having the structure

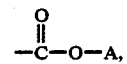

in which A represents an alkyl group of the specified number of carbon atoms.

Examples of such group include carbomethoxy, carboethoxy and the like.

The terms "alkenyl" and "alkynyl" refer to straight and branched chain mono- or polyunsaturated acyclic hydrocarbyl moieties with the number of carbon atoms as specified. Examples of such groups include vinyl, allyl, isopropenyl, isobutenyl, propargyl and the like.

The term "cycloalkyl" refers to saturated cyclic hydrocarbyl moieties having the specified number of carbon atoms and includes cyclopropyl, cyclobutyl, cyclopentyl, cyclohexyl, and cycloheptyl.

The term "haloalkyl" refers to an alkyl group having the indicated number of carbon atoms, substituted by one or more halogen atoms, which may be the same or different. When unspecified, the term "haloalkyl" is meant to refer to alkyl groups ranging from monohaloalkyl to fully substituted haloalkyl groups. Examples of haloalkyl groups include chloromethyl, dichloromethyl, difluoromethyl, trifluoromethyl, 2-chloroethyl, pentafluoroethyl, heptafluoropropyl, 3-chloropropyl, 2,2,2-trifluoro-1-methylethyl, and the like. The term "perhalomethyl" refers to fully halogenated methyl groups such as trifluoromethyl, trichloromethyl, dichlorofluoromethyl and the like.

The heterocyclic rings included in the definition of $R_2$ may be saturated or may be mono- or di-unsaturated. Such rings will contain one or two oxygen or sulfur atoms, for instance, furanyl, tetrahydrofuranyl, tetrahydropyranyl, 1,3-dioxolanyl, 1,3-dioxanyl, 1,4-dioxanyl, tetrahydrothienyl, and the like, optionally substituted with from 1 to 3 methyl groups. In addition or alternatively to the methyl substitution, the or two oxygen or sulfur atoms, for instance, furanyl, tetrahydrofuranyl, tetrahydropyranyl, 1,3-dioxolanyl, 1,3-dioxanyl, 1,4-dioxanyl, tetrahydrothienyl, and the like, optionally substituted with from 1 to 3 methyl groups. In addition or alternatively to the methyl substitution, the heterocyclic ring may have one or more oxygen atoms doubly bonded to carbon or sulfur atoms in the ring.

Polycyclic aliphatic groups include both bi- and tricyclic groups having the indicated number of carbon atoms, for instance the tricyclic adamantyl group.

When it is indicated that a phenyl ring may be di- or further substituted, the substituents may be the same or different, and are selected from the specified groups. When no specific position of substitution is mentioned on a phenyl ring, it is intended that the substituent or substituents may be substituted at any position on the ring.

However, when A is oxygen, substituents on a phenyl ring for R₂ should not be meta-directing electron-withdrawing groups such as nitro or cyano. In such case, the phenyl ring may be substituted with ortho/paradirecting groups (even of the electron-withdrawing type) such as halo, alkoxy and alkyl.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, possessing pre- and/or post-emergence herbicidal activity against various types of weeds including broadleaf and grassy weeds. As mentioned below, some of the compounds demonstrate good control of weeds in certain crops such as rice, wheat, corn and cotton.

Therefore this invention also relates to a method for controlling undesirable vegetation in general comprising applying to a locus where control of such vegetation is desired, either prior or subsequent to the emergence of such vegetation, a herbicidally effective amount of a compound as described herein. In another aspect, the invention also relates to herbicidal compositions comprising a herbicidally effective amount of a compound as described herein, together with an inert diluent or carrier suitable for use with herbicides.

The compounds of this invention can be prepared by reaction of a 2-iminothiazolidine with an acylating agent, an isocyanate (when W is oxygen and A is —NH—) or an isothiocyanate (when W is sulfur and A is —NH—) in the presence of a suitable base according to the reaction

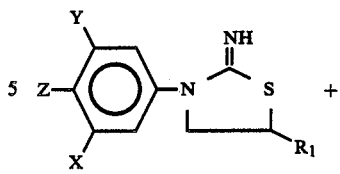

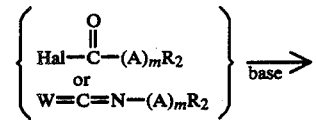

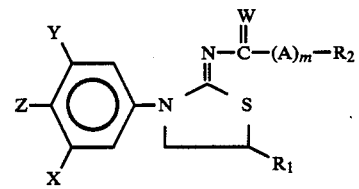

in which Hal stands for halogen, preferably chlorine or bromine. When an acylating agent is used in this step, the reaction is preferably carried out at a temperature of from about 0° to about 10° C. When an isocyanate or an isothiocyanate is used, the reaction is generally conducted at room temperature under nitrogen or other suitable inert gas.

The starting 2-iminothiazolidines may be prepared according to any of several methods as convenient. For instance, U.S. Pat. No. 4,565,083 discloses several methods for production of compounds of this general type, including cyclization of an isothiocyanate and reaction of an iminothiazolidine with a substituted phenyl fluoride. According to another process, as described in Application Ser. No. 214349 of Frank X. Woolard and Charles Kezerian, entitled "Process for Production of 2-Iminothiazolidines and Oxazolidines", filed concurrently herewith, these intermediates can be prepared by reacting an appropriately substituted phenyl cyanamide in a suitable solvent (for instance toluene or methyl ethyl ketone) with an episulfide and a base according to the reaction

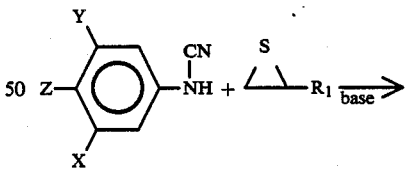

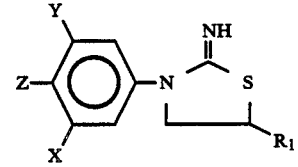

The starting phenyl cyanamides can be made by a number of different methods. These compounds are known in the literature. See, for example, *Organic Synthesis*, Vol. IV, p. 172 and German Patent Application (OLS) 3,538,128.

The examples which follow illustrate production of compounds of this procedure.

EXAMPLE 1

Preparation of 2-(4-Fluorobenzoylimino)-3-(3-trifluoromethyl)phenyl-5-ethylthiazolidine (Compound 12 herein)

3-Trifluoromethylphenyl cyanamide (62.24 g, 0.334 mol), 1,2-butane episulfide (29.48 g, 0.334 mol) and $K_2CO_3$ (46.16 g, 0.334 mole) along with 500 ml methyl ethyl ketone were combined in a flask equipped with a heating mantle, mechanical stirrer, an reflux condenser equipped with a nitrogen bubbler. The solution was stirred and heated to reflux temperature. After 3 hours, the solution was cooled to room temperature, filtered and the solvent removed in vacuo to give a cloudy oil. The oil was taken up in 300 ml ethyl acetate and washed twice with 200 ml $H_2O$, and 150 ml saturated NaCl. It was then dried (over $Na_2SO_4$) and the solvent removed in vacuo to give 73.99 g (81%) of product as a clear yellow oil. The product was identified spectroscopically as 2-imino-3-(3-trifluoromethyl)phenyl-5-ethyl thiazolidine.

To a flask equipped with a magnetic stirrer, thermometer and pressure equalizing addition funnel carrying a nitrogen bubbler, was added 2.50 g (9.1 mmol) of the thiazolidine prepared above, 1.27 ml (9.1 mmol) triethylamine and 25 ml of benzene. The solution was stirred and cooled to 10° C. Thereafter 1.07 (9.1 mmol) of p-fluorobenzoyl chloride in 10 ml of benzene was added dropwise over a five minute period while the solution was stirred under nitrogen until the addition was complete. The suspension was then washed over 50 ml 3% aqueous HCl, twice with 50 ml water, with 50 ml brine, dried (over $MgSO_4$) and the solvent removed in vacuo to give 3.62 g (100%) of product as a thick pale yellow oil. The oil was identified spectroscopically as the subject compound.

EXAMPLE 2

Preparation of 2-(N-Isopropylcarbamoyl)imino-3-(3-trifluoromethyl)-phenyl-5-ethyl thiazolidine (Compound 3 herein)

Two grams (7.3 mmol) of 2-imino-3-(3-trifluoromethyl)phenyl-5-ethylthiazolidine prepared in accordance with the method described in paragraph (1) of Example 1 and 0.72 ml (0.62 g, 7.3 mmol) of isopropyl isocyanate were combined in 30 ml of acetonitrile and stirred overnight under nitrogen at room temperature. Several more drops of the isocyanate were added and the solution stirred for an additional 1.5 hour. The solvent was removed in vacuo to give a yellow-orange syrup that was chromatographed on a silica column in 1:1 ethyl acetate/hexanes to yield 1.41 g (54% of theoretical yield) of product as a caramel colored syrup. The structure was confirmed spectroscopically.

EXAMPLE 3

Preparation of 2-(Isopropoxycarbonyl)imino-3-(3-trifluoromethyl)phenyl-5-ethyl thiazolidine (Compound 4 herein)

To a 500 ml, round-bottomed flask equipped with a stirrer, thermometer, and pressure equalizing addition funnel carrying a nitrogen bubbler was added 18.30 g (66.7 mmol) of 2-imino-3-(3-trifluoromethyl)phenyl-5-ethylthiazolidine prepared in accordance with the method described in paragraph (1) of Example 1 and 200 ml of benzene, plus 5.41 ml (5.28 g, 66.7 mmol) pyridine. The contents were cooled to 5° C. with stirring. Thereafter, 7.60 ml (66.7 mmol) of isopropyl chloroformate in 50 ml of benzene was then added dropwise at such a rate that the temperature did not rise above 10° C. (about 18 min.). The stirring was then continued at 5° C. for 0.5 nhour at which time gas chromatographic analysis showed the reaction to be complete. The reaction suspension was poured into a separation funnel and washed with 4×125 ml of water, 1×125 ml 3% HCl, 1×125 ml brine, dried (over $MgSO_4$) and the solvent removed in vacuo to give 23.18 g (97%) of product was a clear light yellow-orange oil. The structure was confirmed spectroscopically.

Table 1 depicts representative compounds of this invention.

TABLE I

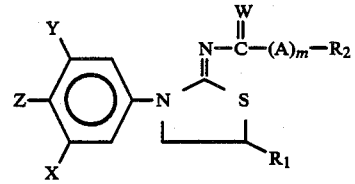

| Cmpd. No. | W | X | Y | Z | $R_1$ | A | $R_2$ | Physical Constant m.p. °C. or $n_D^{30}$ |
|---|---|---|---|---|---|---|---|---|
| 1 | O | $CF_3$ | H | H | $C_2H_5$ | (—) | i-$C_4H_9$ | thick syrup |
| 2 | O | $CF_3$ | H | H | $C_2H_5$ | NH | $CH_3$ | 150.0–153.0 |
| 3 | O | $CF_3$ | H | H | $C_2H_5$ | NH | i-$C_3H_7$ | waxy solid |
| 4 | O | $CF_3$ | H | H | $C_2H_5$ | O | i-$C_3H_7$ | thick syrup |
| 5 | O | $CF_3$ | H | H | $C_2H_5$ | S | i-$C_3H_7$ | 102.0–104.0 |
| 6 | O | $CF_3$ | H | H | $C_2H_5$ | $CH_2$ | $COOC_2H_5$ | thick syrup |
| 7 | O | $CF_3$ | H | H | $C_2H_5$ | (—) | $CH_3$ | 1.5415 |
| 8 | O | $CF_3$ | H | H | $C_2H_5$ | (—) | $CH_2Cl$ | thick syrup |
| 9 | O | $CF_3$ | H | H | $C_2H_5$ | (—) | $CHCl_2$ | thick syrup |
| 10 | O | $CF_3$ | H | H | $C_2H_5$ | $CH_2$ | $OCH_3$ | thick syrup |
| 11 | O | $CF_3$ | H | H | $C_2H_5$ | (—) |  | waxy solid |

TABLE I-continued

| Cmpd. No. | W | X | Y | Z | R₁ | A | R₂ | Physical Constant m.p. °C. or $n_D^{30}$ |
|---|---|---|---|---|---|---|---|---|
| 12 | O | CF₃ | H | H | C₂H₅ | (—) | 2-F—C₆H₄ | thick syrup |
| 13 | O | CF₃ | H | H | C₂H₅ | (—) | 4-F—C₆H₄ | waxy solid |
| 14 | O | CF₃ | H | H | C₂H₅ | O | CH₃ | waxy solid |
| 15 | O | CF₃ | H | H | C₂H₅ | O | C₂H₅ | 1.5336 |
| 16 | O | CF₃ | H | H | C₂H₅ | (—) | —CH=CH₂ | thick syrup |
| 17 | O | CF₃ | H | H | C₂H₅ | (—) | C₂H₅ | 1.5345 |
| 18 | O | CF₃ | H | H | C₂H₅ | (—) | CHClCH₃ | 1.5379 |
| 19 | O | CF₃ | H | H | C₂H₅ | (—) | CH₂CH₂Cl | 1.5393 |
| 20 | O | CF₃ | H | H | C₂H₅ | (—) | CHClCH₂Cl | 1.5512 |
| 21 | O | CF₃ | H | H | C₂H₅ | (—) | CHBrCH₂Br | thick syrup |
| 22 | O | CF₃ | H | H | C₂H₅ | (—) | —C(CH₃)=CH₂ | thick syrup |
| 23 | O | CF₃ | H | H | C₂H₅ | (—) | —CH=CHCH₃ | 1.5559 |
| 24 | O | CF₃ | H | H | C₂H₅ | (—) | —CH=C(CH₃)₂ | waxy solid |
| 25 | O | CF₃ | H | H | C₂H₅ | (—) | —CH₂CH=CH₂ | 1.5746 |
| 26 | O | CF₃ | H | H | C₂H₅ | O | (tetrahydrofuranylmethyl) | thick syrup |
| 27 | O | CF₃ | H | H | C₂H₅ | O | CH(CH₃)COOCH₃ | thick syrup |
| 28 | O | CF₃ | H | H | C₂H₅ | CH₂ | O—C₆H₅ | thick syrup |
| 29 | O | CF₃ | H | H | C₂H₅ | (—) | 3-F—C₆H₄ | waxy solid |
| 30 | O | CF₃ | H | H | C₂H₅ | (—) | CCl₃ | waxy solid |
| 31 | O | CF₃ | H | H | C₂H₅ | (—) | sec-C₄H₉ | 1.5242 |
| 32 | O | CF₃ | H | H | C₂H₅ | (—) | t-C₄H₉ | 81.0–86.5 |
| 33 | O | CF₃ | H | H | C₂H₅ | (—) | CH₂C(CH₃)₃ | 1.5191 |
| 34 | O | CF₃ | H | H | C₂H₅ | (—) | CH(C₂H₅)₂ | 1.5255 |
| 35 | O | CF₃ | H | H | C₂H₅ | (—) | CH₂CH(CH₃)CF₃ | 1.5003 |
| 36 | O | CF₃ | H | H | C₂H₅ | (—) | COOC₂H₅ | waxy solid |
| 37 | O | CF₃ | H | H | C₂H₅ | (—) | (furyl) | waxy solid |
| 38 | O | CF₃ | H | H | C₂H₅ | CH₂ | (cyclopentyl) | 1.5285 |
| 39 | O | CF₃ | H | H | C₂H₅ | (—) | —CH=CHC₆H₅ (trans) | waxy solid |
| 40 | O | CF₃ | H | H | C₂H₅ | CH(CH₃) | —O—C₆H₅ | thick syrup |
| 41 | O | CF₃ | H | H | C₂H₅ | CH₂ | O—(4-Cl—C₆H₄) | thick syrup |
| 42 | O | CF₃ | H | H | C₂H₅ | (—) | 2-CH₃—C₆H₄ | 90.0–95.0 |
| 43 | O | CF₃ | H | H | C₂H₅ | (—) | 2-Cl—C₆H₄ | 97.0–102.0 |
| 44 | O | CF₃ | H | H | C₂H₅ | (—) | 3-Cl—C₆H₄ | thick syrup |
| 45 | O | CF₃ | H | H | C₂H₅ | (—) | 4-Cl—C₆H₄ | 88.0–95.0 |
| 46 | O | CF₃ | H | H | C₂H₅ | (—) | 3-CF₃—C₆H₄ | 62.0–68.0 |
| 47 | O | CF₃ | H | H | C₂H₅ | (—) | 2,6-F—C₆H₃ | thick syrup |
| 48 | O | CF₃ | H | H | C₂H₅ | (—) | CH₂Br | thick syrup |
| 49 | O | CF₃ | H | H | C₂H₅ | (—) | n-C₃H₇ | 1.5400 |
| 50 | O | CF₃ | H | H | C₂H₅ | (—) | C(CH₃)₂CH₂Cl | 65.0–69.0 |
| 51 | O | CF₃ | H | H | C₂H₅ | (—) | —CH(CH₃)C₃H₇ | 1.5315 |
| 52 | O | CF₃ | H | H | C₂H₅ | (—) | —C(CH₃)₂C₃H₇ | 1.5238 |
| 53 | O | CF₃ | H | H | C₂H₅ | (—) | i-C₅H₁₁ | 1.5251 |
| 54 | O | CF₃ | H | H | C₂H₅ | (—) | —CH=CHC₂H₅ (trans) | 1.5451 |
| 55 | O | CF₃ | H | H | C₂H₅ | (—) | (cyclobutyl) | 1.5438 |
| 56 | O | CF₃ | H | H | C₂H₅ | (—) | N(C₂H₅)₂ | 71.0–75.5 |
| 57 | S | CF₃ | H | H | C₂H₅ | (—) | N(CH₃)₂ | 71.0–78.5 |
| 58 | O | CF₃ | H | H | C₂H₅ | (—) | NH₂ | foam |

TABLE I-continued

| Cmpd. No. | W | X | Y | Z | R₁ | A | R₂ | Physical Constant m.p. °C. or $n_D^{30}$ |
|---|---|---|---|---|---|---|---|---|
| 59 | O | CF₃ | H | H | C₂H₅ | (—) | COOCH₃ | 75.5–84.0 |
| 60 | O | CF₃ | H | H | C₂H₅ | O | CH₂CCl₃ | thick syrup |
| 61 | O | Cl | H | F | C₂H₅ | O | i-C₃H₇ | thick syrup |
| 62 | O | CN | H | H | C₂H₅ | O | i-C₃H₇ | thick syrup |
| 63 | O | CF₃ | H | H | C₂H₅ | O | n-C₃H₇ | 1.5196 |
| 64 | O | CF₃ | H | H | C₂H₅ | O | CH₂CH₂Cl | 1.5426 |
| 65 | O | CF₃ | H | H | C₂H₅ | O | CH₂CH(CH₃)₂ | 1.5170 |
| 66 | O | CF₃ | H | H | C₂H₅ | O | CH₂CH=CH₂ | 1.5365 |
| 67 | O | CF₃ | H | H | C₂H₅ | O | n-C₄H₉ | 1.5220 |
| 68 | O | CF₃ | H | H | C₂H₅ | O | CH₂CH₂CH₂Cl | 1.5355 |
| 69 | O | CF₃ | H | H | C₂H₅ | CH₂ | —O—2,4-Cl—C₆H₃ | thick syrup |
| 70 | O | CF₃ | H | F | C₂H₅ | O | C₂H₅ | thick syrup |
| 71 | O | Cl | H | H | C₂H₅ | O | C₂H₅ | 1.5737 |
| 72 | O | CF₃ | H | F | C₂H₅ | O | i-C₃H₇ | thick syrup |
| 73 | O | Cl | H | H | C₂H₅ | O | i-C₃H₇ | 1.5592 |
| 74 | O | CF₃ | H | H | C₂H₅ | O | CCl₃ | 65.0–65.0 |
| 75 | O | CF₃ | H | H | C₂H₅ | S | C₂H₅ | 99.0–104.5 |
| 76 | O | CF₃ | H | H | C₂H₅ | NH | C₂H₅ | thick syrup |
| 77 | O | CF₃ | H | H | C₂H₅ | NH | t-C₄H₉ | 94.0–99.0 |
| 78 | O | CF₃ | H | H | C₂H₅ | NH | n-C₃H₇ | waxy solid |
| 79 | O | CF₃ | H | H | C₂H₅ | NH | CH₂CH=CH₂ | thick syrup |
| 80 | O | CF₃ | H | H | C₂H₅ | NH | n-C₄H₉ | 67.0–79.0 |
| 81 | O | CF₃ | H | H | C₂H₅ | NH | 2-F—C₆H₄ | 118.0–130.0 |
| 82 | O | CF₃ | H | H | C₂H₅ | NH | 3-F—C₆H₄ | 101.5–110.0 |
| 83 | O | CF₃ | H | H | C₂H₅ | NH | 4-F—C₆H₄ | 121.5–128.0 |
| 84 | O | CF₃ | H | H | C₂H₅ | O | sec-C₄H₉ | thick syrup |
| 85 | O | CF₃ | H | H | C₂H₅ | O | CH(C₂H₅)₂ | 67.0–73.0 |
| 86 | O | CF₃ | H | H | C₂H₅ | NH | COCH₂Cl | 102.0–107.0 |
| 87 | S | CF₃ | H | H | C₂H₅ | NH | t-C₄H₉ | 107.0–115.0 |
| 88 | O | CF₃ | H | H | C₂H₅ | S | t-C₄H₉ | 119.0–125.0 |
| 89 | O | CF₃ | H | H | C₂H₅ | S | CH₃ | 103.5–107.0 |
| 90 | O | CF₃ | H | H | C₂H₅ | S | n-C₃H₇ | 60.0–64.0 |
| 91 | O | CF₃ | H | H | C₂H₅ | S | CH₂CH₂Cl | thick syrup |
| 92 | O | CF₃ | H | H | C₂H₅ | S | sec-C₄H₉ | 99.0–106.5 |
| 93 | O | CF₃ | H | H | C₂H₅ | S | i-C₄H₉ | 64.0–72.0 |
| 94 | O | CF₃ | H | H | C₂H₅ | S | n-C₄H₉ | thick syrup |
| 95 | O | CF₃ | H | H | C₂H₅ | S | CH₂CH₂CH₂Cl | thick syrup |
| 96 | O | CF₃ | H | H | C₂H₅ | S | CH₂CHClCH₂Cl | thick syrup |
| 97 | O | CF₃ | H | H | C₂H₅ | CH₂ | 3-CF₃—C₆H₄ | thick syrup |
| 98 | O | NO₂ | H | H | C₂H₅ | O | i-C₃H₇ | thick syrup |
| 99 | O | CF₃ | H | H | C₂H₅ | S | i-C₅H₁₁ | 1.5566 |
| 100 | O | CF₃ | H | H | C₂H₅ | S | CH₂CH(CH₃)CH₂CH₃ | 51.0–54.0 |
| 101 | O | CF₃ | H | H | C₂H₅ | S | n-C₅H₁₁ | 1.5549 |
| 102 | O | CF₃ | H | H | C₂H₅ | (—) | 2-NO₂—C₆H₄ | 106.0–120.0 |
| 103 | O | CF₃ | H | H | C₂H₅ | (—) | 2-CH₃O—C₆H₄ | 113.0–115.0 |
| 104 | O | CF₃ | H | H | C₂H₅ | (—) | 3,4,5-CH₃O—C₆H₂ | thick syrup |
| 105 | O | NO₂ | H | H | C₂H₅ | O | C₂H₅ | waxy solid |
| 106 | O | CF₃ | H | H | C₂H₅ | CH₂ | C₆H₅ | 60.0–63.0 |
| 107 | O | CF₃ | H | H | C₂H₅ | CH₂ | 4-F—C₆H₄ | waxy solid |
| 108 | O | CF₃ | H | H | C₂H₅ | O | C₆H₅ | thick syrup |
| 109 | O | CF₃ | H | H | C₂H₅ | O | 2,4,5-Cl—C₆H₂ | thick syrup |
| 110 | O | CF₃ | H | H | C₂H₅ | O | 4-[C(CH₃)₃]—C₆H₄ | waxy solid |
| 111 | S | CF₃ | H | H | C₂H₅ | NH | C₂H₅ | 160.5–162.0 |
| 112 | S | CF₃ | H | H | C₂H₅ | NH | 2-F—C₆H₄ | 112.0–116.0 |
| 113 | S | CF₃ | H | H | C₂H₅ | NH | 4-F—C₆H₄ | 161.0–166.0 |
| 114 | S | CF₃ | H | H | C₂H₅ | NH | 3-F—C₆H₄ | 159.0–162.5 |
| 115 | S | CF₃ | H | H | C₂H₅ | NH | n-C₃H₇ | 153.0–156.0 |
| 116 | S | CF₃ | H | H | C₂H₅ | NH | i-C₃H₇ | 130.0–135.0 |
| 117 | O | CF₃ | H | H | C₂H₅ | O | cyclopentyl | thick syrup |
| 118 | O | CF₃ | H | H | C₂H₅ | CH₂ | 2-Cl—C₆H₄ | thick syrup |
| 119 | O | CF₃ | H | H | C₂H₅ | CH₂ | 3-Cl—C₆H₄ | thick syrup |
| 120 | O | CF₃ | H | H | C₂H₅ | CH₂ | 4-Cl—C₆H₄ | thick syrup |
| 121 | O | CF₃ | H | H | C₂H₅ | CH₂ | 3,4-Cl—C₆H₃ | thick syrup |
| 122 | O | CF₃ | H | H | C₂H₅ | CH₂ | 3-F—C₆H₄ | 1.5596 |
| 123 | O | CF₃ | H | H | C₂H₅ | CH₂ | 2-F—C₆H₄ | thick syrup |
| 124 | O | CF₃ | H | H | C₂H₅ | CH₂ | 4-CF₃—C₆H₄ | waxy solid |
| 125 | O | CF₃ | H | H | C₂H₅ | CH₂ | 2-CF₃—C₆H₄ | thick syrup |
| 126 | O | CF₃ | H | H | C₂H₅ | CH₂ | 4-NO₂—C₆H₄ | 76.0–91.0 |
| 127 | O | CF₃ | H | H | C₂H₅ | CH₂ | 3-CH₃O—C₆H₄ | 1.5574 |
| 128 | O | CF₃ | H | H | C₂H₅ | CH₂ | 4-CH₃O—C₆H₄ | 1.5574 |

TABLE I-continued

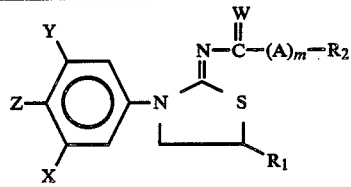

| Cmpd. No. | W | X | Y | Z | $R_1$ | A | $R_2$ | Physical Constant m.p. °C or $n_D^{30}$ |
|---|---|---|---|---|---|---|---|---|
| 129 | O | $CF_3$ | H | H | $C_2H_5$ | $CH(OCH_3)$ | $C_6H_5$ | waxy solid |
| 130 | O | $CF_3$ | H | H | $C_2H_5$ | (—) | α-naphthyl | thick syrup |
| 131 | O | $CF_3$ | H | H | $C_2H_5$ | NH | $COC_6H_5$ | 108.0–120.0 |
| 132 | S | $CF_3$ | H | H | $C_2H_5$ | NH | $COC_6H_5$ | thick syrup |
| 133 | O | $CF_3$ | H | H | $C_2H_5$ | NH | $CH_2CH_2Cl$ | thick syrup |
| 134 | O | $CF_3$ | H | H | $C_2H_5$ | O | $t-C_4H_9$ | 100.0–105.0 |
| 135 | S | $CF_3$ | H | H | $C_2H_5$ | NH | $2-Cl-C_6H_4$ | 85.0–95.0 |
| 136 | S | $CF_3$ | H | H | $C_2H_5$ | NH | $3-Cl-C_6H_4$ | 126.0–132.0 |
| 137 | O | $CF_3$ | H | H | $C_2H_5$ | NH | $3-Cl-C_6H_4$ | thick syrup |
| 138 | S | $CF_3$ | H | H | $C_2H_5$ | NH | $3-CF_3-C_6H_4$ | 112.0–119.0 |
| 139 | O | $CF_3$ | H | H | $C_2H_5$ | NH | $2-CH_3O-C_6H_4$ | 105.0–111.0 |
| 140 | O | $CF_3$ | H | H | $C_2H_5$ | NH | $3-CH_3O-C_6H_4$ | thick syrup |
| 141 | O | $CF_3$ | H | H | $C_2H_5$ | NH | $3-CH_3S-C_6H_4$ | glassy solid |
| 142 | O | $CF_3$ | H | H | $C_2H_5$ | NH | $2,5-F-C_6H_3$ | thick syrup |
| 143 | O | $CF_3$ | H | H | $C_2H_5$ | S | $4-Cl-C_6H_4CH_2$ | waxy solid |
| 144 | O | $CF_3$ | H | H | $C_2H_5$ | $C_2H_4$ | $COOC_2H_5$ | 1.5285 |
| 145 | O | $CF_3$ | H | H | $C_2H_5$ | (—) | $2-Br-C_6H_4$ | 82.0–89.0 |
| 146 | O | $CF_3$ | H | H | $C_2H_5$ | $CH_2$ | $2-CH_3-C_6H_4$ | thick syrup |
| 147 | O | $CF_3$ | H | H | $C_2H_5$ | $CH_2$ | $2-OCH_3-C_6H_4$ | thick syrup |
| 148 | O | $CF_3$ | H | H | $C_2H_5$ | $CH_2$ | $2-NO_2-C_6H_4$ | 100.0–117.0 |
| 149 | S | $CF_3$ | H | H | $C_2H_5$ | NH | $2-Cl-C_6H_4CO-$ | thick syrup |
| 150 | O | $CF_3$ | H | H | $C_2H_5$ | NH | $4-Cl-C_6H_4SO_2-$ | glassy solid |
| 151 | S | $CF_3$ | H | H | $C_2H_5$ | NH | $n-C_4H_9$ | 129.0–138.0 |
| 152 | O | $CF_3$ | H | H | $C_2H_5$ | — | cyclopropyl-$CH_3$ | waxy solid |
| 153 | O | $CF_3$ | H | H | $C_2H_5$ | — | cyclopropyl-$CH_3$ (trans) | thick syrup |
| 154 | O | $CF_3$ | H | H | $C_2H_5$ | $CH_2$ | thienyl (S) | 1.5670 |
| 155 | O | $CF_3$ | H | H | $C_2H_5$ | $CH_2$ | $2,4-Cl-C_6H_4$ | thick syrup |
| 156 | O | $CF_3$ | H | H | $C_2H_5$ | $CH_2$ | $3-NO_2-C_6H_4$ | 95.0–103.0 |
| 157 | O | $CF_3$ | H | H | $C_2H_5$ | $CH_2$ | $3-CH_3-C_6H_4$ | waxy solid |
| 158 | O | $CF_3$ | H | H | $C_2H_5$ | $CH_2$ | $2,6-F-C_6H_3$ | thick syrup |
| 159 | O | $CF_3$ | H | H | $C_2H_5$ | $CH_2$ | $2,6-Cl-C_6H_3$ | waxy solid |
| 160 | O | $CF_3$ | H | H | $C_2H_5$ | NH | $CH_2COOC_2H_5$ | 92.0–99.0 |
| 161 | S | $CF_3$ | H | H | $C_2H_5$ | NH | adamantyl | waxy solid |
| 162 | O | $CF_3$ | H | H | $CONCH_3$ | $CH_3$ | $C_2H_5$ | thick syrup |
| 163 | O | $CF_3$ | H | H | $C_2H_5$ | $CH_2$ | $2,3-(CH_3O)-C_6H_3$ | thick syrup |
| 164 | O | $CF_3$ | H | H | $CH_2Cl$ | O | $i-C_3H_7$ | waxy solid |
| 165 | O | $CF_3$ | H | H | $CH_3$ | O | $i-C_3H_7$ | thick syrup |
| 166 | O | $CF_3$ | H | F | $C_2H_5$ | (—) | cyclopropyl | waxy solid |
| 167 | O | $CF_3$ | H | F | $C_2H_5$ | (—) | cyclopropyl-$CH_3$ | waxy solid |
| 168 | O | $CF_3$ | H | H | $C_2H_5$ | $CH_2$ | $2,3-F-C_6H_3$ | thick syrup |
| 169 | O | $CF_3$ | H | F | $C_2H_5$ | (—) | cyclopropyl-$CH_3$ (trans) | thick syrup |
| 170 | O | $CF_3$ | H | H | $CH_2Cl$ | (—) | $i-C_4H_9$ | thick syrup |
| 171 | O | $CF_3$ | H | H | $CH_2Cl$ | NH | $i-C_3H_7$ | thick syrup |
| 172 | O | $CF_3$ | H | H | $CH_2Cl$ | S | $i-C_3H_7$ | waxy solid |

TABLE I-continued

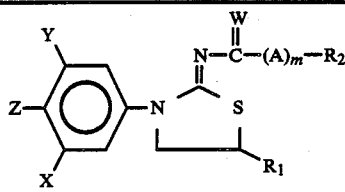

| Cmpd. No. | W | X | Y | Z | R₁ | A | R₂ | Physical Constant m.p. °C. or $n_D^{30}$ |
|---|---|---|---|---|---|---|---|---|
| 173 | O | CF₃ | H | H | CH₃ | (—) | i-C₄H₉ | thick syrup |

(—) Indicates an electron bond, i.e., m = 0.

HERBICIDAL ACTIVITY TESTS

Compounds in Table 1 were tested for herbicidal activity as follows.

The herbicidal effect is observed by comparing the extent of weed control in test flats treated with the compounds against that occurring in similar non-treated control flats. All were applied at 4.0 lb/A (4.48 kg/ha) to pre-emergence and post-emergence screening flats. An 80 gal/A (748.3 l/ha) spray volume was utilized. Post-emergence flats were seeded 12 days prior to treatment. Pre-emergence flats were seeded one day prior to treatment. Overhead watering of pre-emergence flats and soil surface watering of post-emergence flats, so as to avoid wetting the foliage, were carried out for the duration of the test.

Weed seeds were planted in a flat at a seed depth of 0.5 inch (1.3 cm). Soil for flats was prepared using loam soil fortified with 17-17-17 fertilizer (N-P₂O₅-K₂O on a weight basis) and Captan 80W fungicide. The test weeds were as follows:

| COMMON NAME | SCIENTIFIC NAME | ABR |
|---|---|---|
| green foxtail | Setaria viridis | SETVI |
| watergrass | Echinochloa crusgalli | ECHCG |
| wild oat | Avena fatua | AVEFA |
| annual morningglory | Ipomoea purpurea | PHBPU |
| velvetleaf | Abutilon theophrasti | ABUTH |
| wild mustard | Brassica kaber | SINAR |
| yellow nutsedge | Cyperus esculentus | CYPES |

The spray solutions were prepared by dissolving 240 mg of test compound in 20 ml of acetone containing 1% polyoxyethylene sorbitan monolaurate emulsifier, then adding 20 ml of water to the resulting solution. The stock solutions were applied using a linear spray table. Pre-emergence flats are raised to the level of the post-emergence foliage canopy by setting the flats on a wooden block.

In both pre- and post-emergent testing, the degree of weed control was visually assessed, approximately 18 days after treatment, and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in the Table below.

TABLE II

| | | | | | | Percent Injury | | | |
|---|---|---|---|---|---|---|---|---|---|
| Cmpd. No. | Application Rate. (lb/A) | Method | SETVI | ECHCG | AVEFA | PHPBU | ABUTH | SINAR | CYPES |
| 1 | 4.00 | PES | 100 | 100 | 90 | 100 | 100 | 100 | 30 |
|   | 4.00 | POS | 100 | 80 | 80 | 80 | 80 | 70 | 80 |
| 2 | 4.00 | PES | 100 | 100 | 80 | 100 | 100 | 100 | 70 |
|   | 4.00 | POS | 95 | 85 | 60 | 75 | 75 | 80 | 80 |
| 3 | 4.00 | PES | 100 | 100 | 80 | 100 | 100 | 100 | 70 |
|   | 4.00 | POS | 90 | 80 | 70 | 50 | 50 | 80 | 80 |
| 4 | 4.00 | PES | 100 | 90 | 100 | 100 | 100 | 100 | 80 |
|   | 4.00 | POS | 100 | 80 | 80 | 80 | 90 | 50 | 80 |
| 5 | 4.00 | PES | 100 | 70 | 75 | 100 | 75 | 100 | 0 |
|   | 4.00 | POS | 80 | 50 | 50 | 90 | 90 | 60 | 0 |
| 6 | 4.00 | PES | 10 | 10 | 0 | 5 | 5 | 20 | 0 |
|   | 4.00 | POS | 10 | 20 | 10 | 10 | 80 | 80 | 0 |
| 7 | 4.00 | PES | 100 | 40 | 10 | 0 | 0 | 100 | 0 |
|   | 4.00 | POS | 20 | 20 | 20 | 0 | 30 | 80 | 0 |
| 8 | 4.00 | PES | 100 | 30 | 0 | 10 | 0 | 100 | 0 |
|   | 4.00 | POS | 20 | 20 | 0 | 10 | 80 | 100 | 0 |
| 9 | 4.00 | PES | 100 | 30 | 10 | 10 | 80 | 100 | 0 |
|   | 4.00 | POS | 20 | 20 | 20 | 10 | 80 | 100 | 0 |
| 10 | 4.00 | PES | 100 | 100 | 85 | 60 | 100 | 100 | 60 |
|    | 4.00 | POS | 100 | 90 | 80 | 40 | 80 | 100 | 75 |
| 11 | 4.00 | PES | 100 | 100 | 100 | 100 | 100 | 100 | 80 |
|    | 4.00 | POS | 100 | 85 | 85 | 100 | 100 | 100 | 80 |
| 12 | 4.00 | PES | 100 | 100 | 100 | 100 | 100 | 100 | 0 |
|    | 4.00 | POS | 50 | 50 | 50 | 60 | 85 | 90 | 0 |
| 13 | 4.00 | PES | 100 | 30 | 10 | 100 | 100 | 100 | 0 |
|    | 4.00 | POS | 100 | 50 | 50 | 100 | 90 | 100 | 0 |

TABLE II-continued

GREENHOUSE HERBICIDE TEST RESULTS

| Cmpd. No. | Application Rate (lb/A) | Method | Percent Injury | | | | | | |
|---|---|---|---|---|---|---|---|---|---|
| | | | SETVI | ECHCG | AVEFA | PHPBU | ABUTH | SINAR | CYPES |
| 14 | 4.00 | PES | 100 | 100 | 100 | 100 | 100 | 100 | 60 |
| | 4.00 | POS | 100 | 100 | 100 | 100 | 85 | 100 | 20 |
| 15 | 4.00 | PES | 100 | 100 | 95 | 100 | 100 | 100 | 60 |
| | 4.00 | POS | 100 | 80 | 80 | 80 | 80 | 100 | 75 |
| 16 | 4.00 | PES | 100 | 10 | 10 | 40 | 100 | 100 | 0 |
| | 4.00 | POS | 0 | 20 | 0 | 20 | 30 | 80 | 0 |
| 17 | 4.00 | PES | 100 | 100 | 80 | 10 | 90 | 100 | 0 |
| | 4.00 | POS | 100 | 30 | 10 | 10 | 80 | 90 | 0 |
| 18 | 4.00 | PES | 100 | 100 | 20 | 90 | 100 | 100 | 0 |
| | 4.00 | POS | 20 | 20 | 20 | 100 | 80 | 100 | 0 |
| 19 | 4.00 | PES | 100 | 100 | 100 | 100 | 100 | 100 | 0 |
| | 4.00 | POS | 100 | 40 | 40 | 30 | 80 | 90 | 0 |
| 20 | 4.00 | PES | 100 | 20 | 10 | 20 | 95 | 100 | 0 |
| | 4.00 | POS | 10 | 10 | 10 | 10 | 80 | 90 | 0 |
| 21 | 4.00 | PES | 80 | 10 | 0 | 10 | 80 | 100 | 0 |
| | 4.00 | POS | 0 | 0 | 0 | 10 | 10 | 100 | 0 |
| 22 | 4.00 | PES | 100 | 100 | 50 | 80 | 100 | 100 | 0 |
| | 4.00 | POS | 100 | 50 | 50 | 100 | 85 | 100 | 30 |
| 23 | 4.00 | PES | 100 | 100 | 100 | 100 | 100 | 100 | 0 |
| | 4.00 | POS | 100 | 80 | 80 | 80 | 80 | 90 | 70 |
| 24 | 4.00 | PES | 100 | 100 | 100 | 100 | 100 | 100 | 30 |
| | 4.00 | POS | 100 | 85 | 90 | 100 | 90 | 100 | 75 |
| 25 | 4.00 | PES | 100 | 100 | 90 | 100 | 100 | 100 | 0 |
| | 4.00 | POS | 100 | 80 | 80 | 100 | 90 | 100 | 30 |
| 26 | 4.00 | PES | 100 | 100 | 100 | 100 | 100 | 100 | 80 |
| | 4.00 | POS | 100 | 90 | 80 | 100 | 95 | 100 | 80 |
| 27 | 4.00 | PES | 100 | 50 | 50 | 100 | 100 | 100 | 10 |
| | 4.00 | POS | 80 | 50 | 50 | 100 | 100 | 100 | 50 |
| 28 | 4.00 | PES | 100 | 20 | 10 | 20 | 20 | 100 | 0 |
| | 4.00 | POS | 0 | 10 | 0 | 40 | 80 | 90 | 0 |
| 29 | 4.00 | PES | 100 | 85 | 80 | 100 | 100 | 100 | 0 |
| | 4.00 | POS | 10 | 10 | 10 | 60 | 90 | 100 | 0 |
| 30 | 4.00 | PES | 100 | 80 | 60 | 10 | 100 | 100 | 0 |
| | 4.00 | POS | 10 | 10 | 10 | 40 | 40 | 80 | 0 |
| 31 | 4.00 | PES | 100 | 100 | 100 | 100 | 100 | 100 | 0 |
| | 4.00 | POS | 90 | 90 | 90 | 80 | 90 | 90 | 10 |
| 32 | 4.00 | PES | 100 | 100 | 100 | 100 | 100 | 100 | 10 |
| | 4.00 | POS | 100 | 100 | 90 | 80 | 80 | 100 | 0 |
| 33 | 4.00 | PES | 100 | 100 | 100 | 100 | 100 | 100 | 20 |
| | 4.00 | POS | 100 | 90 | 90 | 80 | 80 | 100 | 70 |
| 34 | 4.00 | PES | 100 | 100 | 100 | 100 | 100 | 100 | 10 |
| | 4.00 | POS | 100 | 80 | 80 | 80 | 80 | 100 | 30 |
| 35 | 4.00 | PES | 100 | 100 | 100 | 100 | 100 | 100 | 10 |
| | 4.00 | POS | 100 | 90 | 90 | 80 | 80 | 100 | 60 |
| 36 | 4.00 | PES | 100 | 20 | 10 | 30 | 70 | 100 | 0 |
| | 4.00 | POS | 10 | 10 | 10 | 20 | 20 | 80 | 0 |
| 37 | 4.00 | PES | 100 | 100 | 100 | 100 | 100 | 100 | 0 |
| | 4.00 | POS | 50 | 50 | 50 | 60 | 60 | 80 | 20 |
| 38 | 4.00 | PES | 100 | 100 | 95 | 100 | 100 | 100 | 0 |
| | 4.00 | POS | 100 | 80 | 80 | 80 | 80 | 100 | 20 |
| 39 | 4.00 | PES | 100 | 50 | 20 | 20 | 70 | 100 | 0 |
| | 4.00 | POS | 20 | 20 | 20 | 40 | 60 | 80 | 0 |
| 40 | 4.00 | PES | 100 | 75 | 30 | 40 | 75 | 100 | 0 |
| | 4.00 | POS | 10 | 0 | 0 | 40 | 60 | 80 | 0 |
| 41 | 4.00 | PES | 100 | 80 | 30 | 100 | 100 | 100 | 0 |
| | 4.00 | POS | 50 | 10 | 0 | 100 | 100 | 100 | 0 |
| 42 | 4.00 | PES | 100 | 80 | 70 | 60 | 100 | 100 | 0 |
| | 4.00 | POS | 50 | 50 | 50 | 40 | 60 | 60 | 0 |
| 43 | 4.00 | PES | 100 | 80 | 60 | 100 | 100 | 100 | 0 |
| | 4.00 | POS | 50 | 50 | 50 | 30 | 50 | 80 | 0 |
| 44 | 4.00 | PES | 100 | 50 | 30 | 80 | 100 | 100 | 0 |
| | 4.00 | POS | 30 | 30 | 30 | 40 | 80 | 80 | 0 |
| 45 | 4.00 | PES | 100 | 60 | 30 | 80 | 100 | 100 | 0 |
| | 4.00 | POS | 30 | 30 | 30 | 30 | 30 | 80 | 0 |
| 46 | 4.00 | PES | 100 | 40 | 30 | 70 | 85 | 100 | 0 |
| | 4.00 | POS | 30 | 80 | 30 | 60 | 80 | 80 | 0 |
| 47 | 4.00 | PES | 100 | 30 | 10 | 60 | 100 | 100 | 0 |
| | 4.00 | POS | 30 | 30 | 30 | 40 | 60 | 80 | 0 |
| 48 | 4.00 | PES | 100 | 20 | 0 | 10 | 0 | 100 | 0 |
| | 4.00 | POS | 30 | 30 | 30 | 60 | 60 | 80 | 0 |
| 49 | 4.00 | PES | 100 | 100 | 95 | 95 | 100 | 100 | 0 |
| | 4.00 | POS | 80 | 30 | 60 | 40 | 80 | 80 | 0 |
| 50 | 4.00 | PES | 100 | 100 | 80 | 100 | 100 | 100 | 0 |
| | 4.00 | POS | 80 | 80 | 60 | 80 | 80 | 80 | 10 |
| 51 | 4.00 | PES | 100 | 100 | 85 | 100 | 100 | 100 | 0 |
| | 4.00 | POS | 100 | 80 | 80 | 90 | 85 | 100 | 30 |
| 51 | 4.00 | PES | 100 | 100 | 85 | 100 | 100 | 100 | 0 |

TABLE II-continued
GREENHOUSE HERBICIDE TEST RESULTS

| Cmpd. No. | Application Rate (lb/A) | Method | Percent Injury | | | | | | |
|---|---|---|---|---|---|---|---|---|---|
| | | | SETVI | ECHCG | AVEFA | PHPBU | ABUTH | SINAR | CYPES |
| | 4.00 | POS | 100 | 80 | 80 | 90 | 85 | 100 | 30 |
| 52 | 4.00 | PES | 100 | 100 | 30 | 80 | 100 | 100 | 0 |
| | 4.00 | POS | 100 | 90 | 80 | 90 | 90 | 90 | 0 |
| 53 | 4.00 | PES | 100 | 100 | 80 | 100 | 100 | 100 | 0 |
| | 4.00 | POS | 100 | 90 | 80 | 95 | 100 | 100 | 0 |
| 54 | 4.00 | PES | 100 | 100 | 50 | 75 | 100 | 100 | 0 |
| | 4.00 | POS | 100 | 85 | 50 | 85 | 85 | 100 | 0 |
| 55 | 4.00 | PES | 100 | 100 | 95 | 100 | 100 | 100 | 0 |
| | 4.00 | POS | 100 | 85 | 80 | 100 | 100 | 100 | 30 |
| 56 | 4.00 | PES | 100 | 100 | 100 | 100 | 100 | 100 | 0 |
| | 4.00 | POS | 100 | 90 | 85 | 80 | 80 | 80 | 60 |
| 57 | 4.00 | PES | 100 | 100 | 100 | 100 | 100 | 100 | 30 |
| | 4.00 | POS | 100 | 100 | 90 | 85 | 90 | 100 | 70 |
| 58 | 4.00 | PES | 100 | 100 | 90 | 100 | 100 | 100 | 80 |
| | 4.00 | POS | 100 | 85 | 80 | 80 | 80 | 100 | 80 |
| 59 | 4.00 | PES | 100 | 0 | 0 | 10 | 10 | 100 | 0 |
| | 4.00 | POS | 0 | 10 | 0 | 20 | 30 | 80 | 0 |
| 60 | 4.00 | PES | 100 | 10 | 30 | 0 | 100 | 100 | 0 |
| | 4.00 | POS | 10 | 10 | 10 | 20 | 50 | 90 | 0 |
| 61 | 4.00 | PES | 100 | 100 | 100 | 100 | 100 | 100 | 70 |
| | 4.00 | POS | 100 | 100 | 100 | 90 | 100 | 90 | 80 |
| 62 | 4.00 | PES | 100 | 100 | 100 | 100 | 100 | 100 | 80 |
| | 4.00 | POS | 100 | 100 | 90 | 100 | 100 | 100 | 80 |
| 63 | 4.00 | PES | 100 | 100 | 100 | 100 | 100 | 100 | 30 |
| | 4.00 | POS | 100 | 90 | 80 | 90 | 90 | 80 | 70 |
| 64 | 4.00 | PES | 100 | 100 | 80 | 100 | 100 | 100 | 0 |
| | 4.00 | POS | 100 | 100 | 80 | 80 | 80 | 80 | 70 |
| 65 | 4.00 | PES | 100 | 100 | 100 | 100 | 100 | 100 | 0 |
| | 4.00 | POS | 100 | 90 | 90 | 80 | 95 | 90 | 70 |
| 66 | 4.00 | PES | 100 | 90 | 100 | 100 | 100 | 100 | 50 |
| | 4.00 | POS | 100 | 80 | 80 | 60 | 80 | 90 | 80 |
| 67 | 4.00 | PES | 100 | 60 | 40 | 100 | 100 | 100 | 0 |
| | 4.00 | POS | 100 | 50 | 50 | 70 | 80 | 90 | 30 |
| 68 | 4.00 | PES | 100 | 80 | 0 | 100 | 100 | 100 | 0 |
| | 4.00 | POS | 100 | 50 | 50 | 60 | 80 | 90 | 50 |
| 69 | 4.00 | PES | 100 | 80 | 0 | 100 | 80 | 100 | 0 |
| | 4.00 | POS | 10 | 10 | 10 | 100 | 100 | 100 | 0 |
| 70 | 4.00 | PES | 100 | 100 | 100 | 100 | 100 | 100 | 80 |
| | 4.00 | POS | 100 | 100 | 95 | 75 | 90 | 100 | 90 |
| 71 | 4.00 | PES | 100 | 100 | 95 | 100 | 20 | 100 | 70 |
| | 4.00 | POS | 100 | 100 | 60 | 60 | 80 | 100 | 75 |
| 72 | 4.00 | PES | 100 | 100 | 100 | 100 | 100 | 100 | 80 |
| | 4.00 | POS | 100 | 90 | 80 | 80 | 80 | 80 | 80 |
| 73 | 4.00 | PES | 100 | 100 | 100 | 100 | 100 | 100 | 70 |
| | 4.00 | POS | 100 | 95 | 95 | 90 | 85 | 100 | 80 |
| 74 | 4.00 | PES | 100 | 90 | 50 | 20 | 20 | 100 | 0 |
| | 4.00 | POS | 50 | 50 | 50 | 60 | 60 | 80 | 20 |
| 75 | 4.00 | PES | 100 | 100 | 95 | 100 | 100 | 100 | 0 |
| | 4.00 | POS | 80 | 60 | 50 | 40 | 80 | 80 | 0 |
| 76 | 4.00 | PES | 100 | 100 | 100 | 100 | 100 | 100 | 80 |
| | 4.00 | POS | 100 | 100 | 100 | 90 | 90 | 100 | 80 |
| 77 | 4.00 | PES | 100 | 100 | 100 | 100 | 100 | 100 | 80 |
| | 4.00 | POS | 100 | 100 | 100 | 100 | 100 | 100 | 80 |
| 78 | 4.00 | PES | 100 | 100 | 100 | 100 | 100 | 100 | 70 |
| | 4.00 | POS | 100 | 90 | 100 | 80 | 80 | 100 | 80 |
| 79 | 4.00 | PES | 100 | 100 | 100 | 100 | 100 | 100 | 70 |
| | 4.00 | POS | 80 | 80 | 80 | 80 | 80 | 80 | 80 |
| 80 | 4.00 | PES | 100 | 100 | 100 | 100 | 100 | 100 | 70 |
| | 4.00 | POS | 80 | 70 | 75 | 80 | 80 | 80 | 80 |
| 81 | 4.00 | PES | 100 | 50 | 50 | 100 | 100 | 100 | 0 |
| | 4.00 | POS | 50 | 50 | 50 | 20 | 50 | 80 | 0 |
| 82 | 4.00 | PES | 100 | 60 | 40 | 100 | 100 | 100 | 0 |
| | 4.00 | POS | 50 | 50 | 50 | 20 | 60 | 80 | 0 |
| 83 | 4.00 | PES | 100 | 30 | 30 | 100 | 100 | 100 | 0 |
| | 4.00 | POS | 0 | 0 | 0 | 40 | 80 | 80 | 0 |
| 84 | 4.00 | PES | 100 | 100 | 100 | 100 | 100 | 100 | 80 |
| | 4.00 | POS | 100 | 90 | 80 | 80 | 80 | 80 | 80 |
| 85 | 4.00 | PES | 100 | 100 | 90 | 100 | 100 | 100 | 0 |
| | 4.00 | POS | 50 | 60 | 50 | 80 | 80 | 80 | 50 |
| 86 | 4.00 | PES | 100 | 100 | 100 | 100 | 100 | 100 | 80 |
| | 4.00 | POS | 100 | 80 | 60 | 80 | 80 | 80 | 80 |
| 87 | 4.00 | PES | 100 | 100 | 100 | 100 | 100 | 100 | 70 |
| | 4.00 | POS | 100 | 90 | 90 | 80 | 90 | 90 | 80 |
| 88 | 4.00 | PES | 100 | 80 | 75 | 90 | 100 | 100 | 0 |
| | 4.00 | POS | 20 | 20 | 20 | 30 | 30 | 50 | 0 |
| 89 | 4.00 | PES | 100 | 100 | 100 | 100 | 100 | 100 | 30 |
| | 4.00 | POS | 100 | 80 | 80 | 60 | 80 | 80 | 80 |

TABLE II-continued

GREENHOUSE HERBICIDE TEST RESULTS

| Cmpd. No. | Application Rate (lb/A) | Method | Percent Injury | | | | | | |
|---|---|---|---|---|---|---|---|---|---|
| | | | SETVI | ECHCG | AVEFA | PHPBU | ABUTH | SINAR | CYPES |
| 90 | 4.00 | PES | 100 | 100 | 100 | 100 | 100 | 100 | 0 |
| | 4.00 | POS | 80 | 30 | 60 | 60 | 80 | 90 | 20 |
| 91 | 4.00 | PES | 100 | 100 | 90 | 100 | 100 | 100 | 0 |
| | 4.00 | POS | 100 | 50 | 50 | 60 | 80 | 80 | 80 |
| 92 | 4.00 | PES | 100 | 30 | 80 | 100 | 100 | 100 | 0 |
| | 4.00 | POS | 20 | 20 | 20 | 30 | 50 | 100 | 0 |
| 93 | 4.00 | PES | 100 | 50 | 100 | 100 | 100 | 100 | 0 |
| | 4.00 | POS | 80 | 30 | 50 | 60 | 80 | 80 | 0 |
| 94 | 4.00 | PES | 100 | 75 | 90 | 100 | 100 | 100 | 0 |
| | 4.00 | POS | 20 | 20 | 20 | 60 | 80 | 80 | 0 |
| 95 | 4.00 | PES | 100 | 20 | 80 | 100 | 100 | 100 | 0 |
| | 4.00 | POS | 20 | 30 | 20 | 80 | 80 | 80 | 0 |
| 96 | 4.00 | PES | 100 | 20 | 40 | 100 | 100 | 100 | 0 |
| | 4.00 | POS | 20 | 20 | 20 | 40 | 80 | 80 | 0 |
| 97 | 4.00 | PES | 100 | 50 | 40 | 100 | 100 | 100 | 0 |
| | 4.00 | POS | 30 | 30 | 20 | 60 | 80 | 80 | 0 |
| 98 | 4.00 | PES | 100 | 100 | 100 | 100 | 100 | 100 | 80 |
| | 4.00 | POS | 100 | 80 | 80 | 80 | 80 | 100 | 80 |
| 99 | 4.00 | PES | 100 | 100 | 30 | 100 | 100 | 100 | 0 |
| | 4.00 | POS | 20 | 20 | 20 | 40 | 50 | 80 | 0 |
| 100 | 4.00 | PES | 100 | 50 | 30 | 100 | 100 | 100 | 0 |
| | 4.00 | POS | 20 | 20 | 20 | 50 | 60 | 100 | 0 |
| 101 | 4.00 | PES | 100 | 20 | 20 | 100 | 80 | 100 | 0 |
| | 4.00 | POS | 20 | 0 | 0 | 20 | 50 | 100 | 0 |
| 102 | 4.00 | PES | 20 | 20 | 20 | 40 | 100 | 100 | 0 |
| | 4.00 | POS | 50 | 20 | 20 | 30 | 50 | 80 | 0 |
| 103 | 4.00 | PES | 100 | 30 | 20 | 90 | 100 | 100 | 0 |
| | 4.00 | POS | 20 | 20 | 20 | 30 | 50 | 100 | 0 |
| 104 | 4.00 | PES | 100 | 0 | 10 | 20 | 20 | 100 | 0 |
| | 4.00 | POS | 0 | 0 | 0 | 20 | 30 | 100 | 0 |
| 105 | 4.00 | PES | 100 | 75 | 60 | 10 | 100 | 100 | 30 |
| | 4.00 | POS | 100 | 80 | 80 | 40 | 60 | 100 | 80 |
| 106 | 4.00 | PES | 100 | 100 | 90 | 100 | 100 | 100 | 0 |
| | 4.00 | POS | 100 | 80 | 80 | 60 | 80 | 100 | 30 |
| 107 | 4.00 | PES | 100 | 100 | 85 | 100 | 100 | 100 | 0 |
| | 4.00 | POS | 100 | 60 | 50 | 60 | 60 | 100 | 0 |
| 108 | 4.00 | PES | 100 | 10 | 10 | 10 | 10 | 100 | 0 |
| | 4.00 | POS | 0 | 0 | 0 | 10 | 0 | 100 | 0 |
| 109 | 4.00 | PES | 100 | 0 | 0 | 10 | 10 | 100 | 0 |
| | 4.00 | POS | 0 | 0 | 0 | 10 | 20 | 80 | 0 |
| 110 | 4.00 | PES | 100 | 10 | 0 | 20 | 30 | 100 | 0 |
| | 4.00 | POS | 0 | 0 | 0 | 10 | 10 | 80 | 0 |
| 111 | 4.00 | PES | 100 | 90 | 95 | 100 | 85 | 100 | 0 |
| | 4.00 | POS | 100 | 80 | 80 | 60 | 80 | 100 | 80 |
| 112 | 4.00 | PES | 100 | 20 | 20 | 20 | 60 | 100 | 0 |
| | 4.00 | POS | 30 | 30 | 30 | 30 | 50 | 80 | 0 |
| 113 | 4.00 | PES | 100 | 10 | 0 | 10 | 10 | 100 | 0 |
| | 4.00 | POS | 0 | 0 | 0 | 0 | 0 | 20 | 0 |
| 114 | 4.00 | PES | 100 | 10 | 10 | 20 | 20 | 100 | 0 |
| | 4.00 | POS | 10 | 10 | 0 | 30 | 50 | 50 | 0 |
| 115 | 4.00 | PES | 100 | 100 | 70 | 100 | 100 | 100 | 0 |
| | 4.00 | POS | 60 | 60 | 60 | 60 | 60 | 100 | 50 |
| 116 | 4.00 | PES | 100 | 100 | 80 | 100 | 100 | 100 | 0 |
| | 4.00 | POS | 80 | 90 | 80 | 80 | 60 | 90 | 80 |
| 117 | 4.00 | PES | 100 | 100 | 80 | 100 | 100 | 100 | 0 |
| | 4.00 | POS | 80 | 90 | 80 | 80 | 80 | 100 | 80 |
| 118 | 4.00 | PES | 100 | 100 | 80 | 100 | 100 | 100 | 0 |
| | 4.00 | POS | 100 | 90 | 70 | 100 | 100 | 100 | 0 |
| 119 | 4.00 | PES | 100 | 100 | 80 | 100 | 100 | 100 | 0 |
| | 4.00 | POS | 100 | 90 | 80 | 80 | 80 | 100 | 0 |
| 120 | 4.00 | PES | 100 | 100 | 70 | 100 | 100 | 100 | 0 |
| | 4.00 | POS | 100 | 95 | 40 | 60 | 80 | 100 | 0 |
| 121 | 4.00 | PES | 100 | 10 | 10 | 40 | 20 | 100 | 0 |
| | 4.00 | POS | 20 | 20 | 20 | 40 | 40 | 80 | 0 |
| 122 | 4.00 | PES | 100 | 100 | 85 | 100 | 100 | 100 | 0 |
| | 4.00 | POS | 100 | 100 | 80 | 90 | 90 | 100 | 0 |
| 123 | 4.00 | PES | 100 | 100 | 90 | 100 | 100 | 100 | 0 |
| | 4.00 | POS | 100 | 100 | 60 | 100 | 100 | 100 | 20 |
| 124 | 4.00 | PES | 100 | 90 | 20 | 20 | 80 | 100 | 0 |
| | 4.00 | POS | 20 | 80 | 20 | 10 | 30 | 100 | 0 |
| 125 | 4.00 | PES | 100 | 30 | 20 | 40 | 60 | 100 | 0 |
| | 4.00 | POS | 100 | 30 | 30 | 60 | 50 | 80 | 0 |
| 126 | 4.00 | PES | 100 | 10 | 10 | 10 | 20 | 80 | 0 |
| | 4.00 | POS | 20 | 20 | 0 | 20 | 20 | 100 | 0 |
| 127 | 4.00 | PES | 100 | 100 | 75 | 100 | 85 | 100 | 0 |
| | 4.00 | POS | 100 | 50 | 30 | 80 | 80 | 100 | 0 |
| 128 | 4.00 | PES | 100 | 100 | 90 | 100 | 100 | 100 | 0 |

TABLE II-continued
GREENHOUSE HERBICIDE TEST RESULTS

| Cmpd. No. | Application Rate (lb/A) | Method | Percent Injury | | | | | | |
|---|---|---|---|---|---|---|---|---|---|
| | | | SETVI | ECHCG | AVEFA | PHPBU | ABUTH | SINAR | CYPES |
| | 4.00 | POS | 100 | 100 | 80 | 60 | 80 | 80 | 0 |
| 129 | 4.00 | PES | 100 | 40 | 20 | 40 | 80 | 100 | 0 |
| | 4.00 | POS | 100 | 30 | 20 | 60 | 50 | 100 | 0 |
| 130 | 4.00 | PES | 100 | 10 | 10 | 10 | 60 | 100 | 0 |
| | 4.00 | POS | 0 | 10 | 0 | 40 | 60 | 100 | 0 |
| 131 | 4.00 | PES | 100 | 10 | 10 | 10 | 75 | 100 | 0 |
| | 4.00 | POS | 20 | 30 | 20 | 80 | 80 | 100 | 0 |
| 132 | 4.00 | PES | 100 | 20 | 40 | 40 | 60 | 100 | 0 |
| | 4.00 | POS | 90 | 50 | 40 | 85 | 80 | 100 | 50 |
| 133 | 4.00 | PES | 100 | 100 | 20 | 60 | 80 | 85 | 0 |
| | 4.00 | POS | 80 | 30 | 30 | 100 | 100 | 85 | 0 |
| 134 | 4.00 | PES | 100 | 100 | 100 | 80 | 100 | 100 | 0 |
| | 4.00 | POS | 100 | 30 | 10 | 100 | 100 | 100 | 0 |
| 135 | 4.00 | PES | 100 | 20 | 20 | 60 | 100 | 100 | 0 |
| | 4.00 | POS | 70 | 20 | 10 | 40 | 100 | 80 | 0 |
| 136 | 4.00 | PES | 100 | 0 | 0 | 20 | 20 | 50 | 0 |
| | 4.00 | POS | 10 | 10 | 0 | 40 | 70 | 80 | 0 |
| 137 | 4.00 | PES | 100 | 20 | 20 | 80 | 80 | 100 | 0 |
| | 4.00 | POS | 75 | 20 | 0 | 60 | 80 | 80 | 0 |
| 138 | 4.00 | PES | 100 | 0 | 0 | 0 | 0 | 0 | 0 |
| | 4.00 | POS | 10 | 10 | 10 | 20 | 30 | 30 | 0 |
| 139 | 4.00 | PES | 100 | 0 | 10 | 10 | 20 | 20 | 0 |
| | 4.00 | POS | 10 | 0 | 0 | 40 | 20 | 50 | 0 |
| 140 | 4.00 | PES | 100 | 30 | 30 | 75 | 100 | 100 | 0 |
| | 4.00 | POS | 10 | 10 | 0 | 40 | 80 | 90 | 0 |
| 141 | 4.00 | PES | 100 | 20 | 20 | 75 | 20 | 100 | 0 |
| | 4.00 | POS | 20 | 10 | 0 | 100 | 90 | 90 | 0 |
| 142 | 4.00 | PES | 100 | 100 | 75 | 100 | 100 | 100 | 0 |
| | 4.00 | POS | 60 | 50 | 30 | 100 | 80 | 80 | 0 |
| 143 | 4.00 | PES | 80 | 0 | 0 | 0 | 0 | 80 | 0 |
| | 4.00 | POS | 10 | 10 | 10 | 10 | 80 | 80 | 0 |
| 144 | 4.00 | PES | 20 | 0 | 0 | 0 | 0 | 0 | 0 |
| | 4.00 | POS | 0 | 0 | 0 | 20 | 50 | 80 | 0 |
| 145 | 4.00 | PES | 100 | 60 | 30 | 60 | 85 | 100 | 0 |
| | 4.00 | POS | 20 | 30 | 20 | 60 | 80 | 80 | 0 |
| 146 | 4.00 | PES | 100 | 100 | 60 | 85 | 90 | 100 | 0 |
| | 4.00 | POS | 80 | 50 | 50 | 80 | 80 | 80 | 0 |
| 147 | 4.00 | PES | 100 | 100 | 60 | 70 | 100 | 100 | 0 |
| | 4.00 | POS | 80 | 50 | 50 | 80 | 80 | 80 | 0 |
| 148 | 4.00 | PES | 100 | 75 | 20 | 70 | 100 | 100 | 0 |
| | 4.00 | POS | 10 | 10 | 10 | 80 | 90 | 90 | 0 |
| 149 | 4.00 | PES | 100 | 95 | 50 | 40 | 90 | 100 | 30 |
| | 4.00 | POS | 80 | 50 | 50 | 80 | 80 | 80 | 30 |
| 150 | 4.00 | PES | 80 | 0 | 0 | 0 | 10 | 30 | 0 |
| | 4.00 | POS | 0 | 0 | 0 | 20 | 60 | 80 | 0 |
| 151 | 4.00 | PES | 100 | 30 | 30 | 40 | 50 | 100 | 0 |
| | 4.00 | POS | 30 | 30 | 20 | 80 | 80 | 80 | 0 |
| 152 | 4.00 | PES | 100 | 100 | 100 | 100 | 100 | 100 | 30 |
| | 4.00 | POS | 100 | 80 | 80 | 80 | 80 | 80 | 0 |
| 153 | 4.00 | PES | 100 | 100 | 90 | 100 | 100 | 100 | 30 |
| | 4.00 | POS | 100 | 80 | 80 | 80 | 80 | 90 | 30 |
| 154 | 4.00 | PES | 100 | 100 | 85 | 95 | 100 | 100 | 0 |
| | 4.00 | POS | 90 | 60 | 50 | 100 | 85 | 100 | 0 |
| 155 | 4.00 | PES | 100 | 85 | 60 | 85 | 100 | 100 | 0 |
| | 4.00 | POS | 60 | 40 | 30 | 80 | 80 | 80 | 0 |
| 156 | 4.00 | PES | 100 | 20 | 10 | 40 | 70 | 95 | 0 |
| | 4.00 | POS | 20 | 20 | 20 | 60 | 60 | 80 | 0 |
| 157 | 4.00 | PES | 100 | 100 | 80 | 85 | 100 | 100 | 0 |
| | 4.00 | POS | 80 | 40 | 30 | 60 | 80 | 80 | 0 |
| 158 | 4.00 | PES | 100 | 100 | 90 | 100 | 100 | 100 | 0 |
| | 4.00 | POS | 100 | 100 | 85 | 85 | 90 | 80 | 0 |
| 159 | 4.00 | PES | 100 | 100 | 50 | 80 | 100 | 85 | 0 |
| | 4.00 | POS | 80 | 30 | 20 | 80 | 85 | 90 | 20 |
| 160 | 4.00 | PES | 75 | 20 | 0 | 5 | 0 | 0 | 0 |
| | 4.00 | POS | 0 | 0 | 0 | 50 | 20 | 100 | 0 |
| 161 | 4.00 | PES | 100 | 30 | 20 | 20 | 60 | 100 | 0 |
| | 4.00 | POS | 70 | 30 | 20 | 40 | 80 | 100 | 0 |
| 162 | 4.00 | PES | 100 | 60 | 20 | 20 | 0 | 100 | 0 |
| | 4.00 | POS | 100 | 0 | 0 | 30 | 40 | 80 | 0 |
| 163 | 4.00 | PES | 100 | 20 | 10 | 20 | 10 | 100 | 0 |
| | 4.00 | POS | 100 | 10 | 10 | 20 | 40 | 85 | 0 |
| 164 | 4.00 | PES | 100 | 100 | 95 | 100 | 100 | 100 | 20 |
| | 4.00 | POS | 100 | 100 | 100 | 100 | 100 | 100 | 70 |
| 165 | 4.00 | PES | 100 | 100 | 100 | 100 | 100 | 100 | 80 |
| | 4.00 | POS | 100 | 95 | 100 | 80 | 80 | 80 | 80 |
| 166 | 4.00 | PES | 100 | 100 | 100 | 100 | 95 | 100 | N |
| | 4.00 | POS | 100 | 100 | 100 | 100 | 100 | 100 | 80 |

TABLE II-continued
GREENHOUSE HERBICIDE TEST RESULTS

| Cmpd. No. | Application Rate (lb/A) | Method | Percent Injury | | | | | | |
|---|---|---|---|---|---|---|---|---|---|
| | | | SETVI | ECHCG | AVEFA | PHPBU | ABUTH | SINAR | CYPES |
| 167 | 4.00 | PES | 100 | 100 | 100 | 100 | 100 | 100 | 0 |
| | 4.00 | POS | 100 | 100 | 100 | 90 | 95 | 100 | 20 |
| 168 | 4.00 | PES | 100 | 100 | 95 | 100 | 95 | 100 | 0 |
| | 4.00 | POS | 100 | 70 | 70 | 80 | 80 | 80 | 10 |
| 169 | 4.00 | PES | 100 | 100 | 95 | 100 | 100 | 100 | 0 |
| | 4.00 | POS | 100 | 90 | 100 | 95 | 95 | 100 | 20 |
| 170 | 4.00 | PES | 100 | 100 | 70 | 100 | 95 | 100 | 90 |
| | 4.00 | POS | 100 | 90 | 30 | 90 | 90 | 90 | 0 |
| 171 | 4.00 | PES | 100 | 100 | 40 | 100 | 100 | 100 | 20 |
| | 4.00 | POS | 100 | 100 | 100 | 95 | 100 | 100 | 80 |
| 172 | 4.00 | PES | 100 | 100 | 30 | 50 | 100 | 100 | 0 |
| | 4.00 | POS | 60 | 30 | 20 | 10 | 20 | 80 | 0 |
| 173 | 4.00 | PES | 100 | 100 | 85 | 100 | 100 | 100 | 0 |
| | 4.00 | POS | 100 | 90 | 85 | 90 | 90 | 90 | 0 |

FURTHER HERBICIDAL EVALUATION

Compounds showing good activity in the evaluations described above were submitted for one or more subsequent evaluations involving, for example, different weeds, lower application rates, varying application procedures, and/or selectivity with respect to crops. The weeds employed in these tests included those utilized in the tests just described, as well as a number of others such as one or more species of ryegrass (Lolium), Sorghum, signalgrass (Brachiaria), cocklebur (Xanthium), Sesbania, Cassia, Alopecurus, oats (Avena), bluegrass (Poa), Matricaria, chickweed (Stellaria), bedstraw (Galium), and violet Viola). Crops which were variously employed in these evaluations included cotton (Gossypium hirsutum), soybean (Glycine max), corn (Zea maize), milo (Sorghum bicolor), wheat (Tritium aestivum), sugarbeet (Beta vulgaris), rice (Oryza sativa), carrot (Daucus carota), and barley (Hordeum vulgare).

In summation, compounds submitted for further evaluation showed varying activity depending on the compound and the evaluation employed. Some compounds showed a better activity in controlling grasses, others in controlling broadleaf weeds. Some compounds demonstrated better activity in pre-emergence application, others in post-emergence application. Some compounds demonstrated good activity in nearly all types of application. Some compounds demonstrated good control in tests at application rates ranging as low as 0.06 pound per acre (0.065 kg/ha).

With respect to injury to crops, nearly all compounds tested produced unacceptable injury to sugarbeets even at relatively low levels of application. Some compounds showed good broad-spectrum activity but relatively low selectivity, causing injury to both weeds and crops in the same tests. Other compounds showed varying selectivity to certain crops, particularly cereals, such as wheat, rice and corn, most notably with respect to rice in various methods of application. A number of compounds also demonstrated selectivity in controlling weeds in the presence of cotton.

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, tablets, powders and the like. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives, thickeners, binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic materials such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| Oil | |
|---|---|
| Ingredient | Weight % |
| Active Compound | 1 |
| Oil solvent-heavy aromatic naphtha | 99 |
| Total | 100 |
| Emulsifiable Concentrate | |
| Active Compound | 50 |
| Kerosene | 45 |
| Emulsifying agent (mixture of long chain ethoxylated polyethers with long chain sulfonate) | 5 |

| -continued | |
|---|---|
| Total | 100 |
| Emulsifiable Concentrate | |
| Active Compound | 90 |
| Kerosene | 5 |
| Emulsifying agent (mixture of long chain ethoxylated polyethers with long chain sulfonate) | 5 |
| Total | 100 |

| Dusts and/or Powders | | | |
|---|---|---|---|
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:
1. A compound having the formula

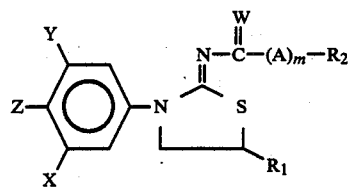

in which
W is oxygen or sulfur;
X is hydrogen, halogen, nitro, cyano, perhalomethyl, difluoromethyl, pentafluoroethyl, $C_1$-$C_4$ alkyl, $C_1$-$C_4$ alkoxy, trifluoromethylthio, difluoromethoxy, trifluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$-$C_4$ alkyloximinomethyl, benzyloximinomethyl, 1-($C_1$-$C_4$ alkyl)oximinoethyl and 1-benzyloximinoethyl;
Y is hydrogen, halogen, nitro, cyano, perhalomethyl, difluoromethyl, pentafluoroethyl, $C_1$-$C_4$ alkyl, $C_1$-$C_4$ alkoxy, trifluoromethylthio, trifluoromethoxy, tetrafluoroethoxy, methylsulfonyl and trifluoromethylsulfonyl;
Z is hydrogen or fluoro if Y is hydrogen, or hydrogen if Y is other than hydrogen;
$R_1$ is hydrogen, methyl, ethyl or chloromethyl;
A is oxygen, sulfur,

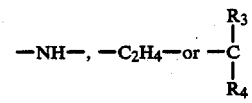

in which $R_3$ and $R_4$ are independently hydrogen, methyl or methoxy; and
$R_2$ is $C_1$-$C_6$ alkyl; carbo($C_1$-$C_6$)-alkoxy; carbo($C_1$-$C_6$)alkoxy($C_1$-$C_2$ alkylene); $C_1$-$C_4$ haloalkyl if m is 1; $C_2$-$C_4$ haloalkyl if m is 0; $C_1$-$C_5$ alkoxy; $C_3$-$C_6$ cycloalkyl optionally substituted by up to 2 methyl groups; $C_2$-$C_6$ alkenyl; phenyl; substituted phenyl in which the substituents are $C_1$-$C_4$ alkyl, halogen, trifluoromethyl, nitro, $C_1$-$C_4$ alkoxy, $C_1$-$C_4$ alkylthio, or cyano; phenoxy; halosubstituted phenoxy; styryl; p-chlorophenylsulfonyl; $C_2$-$C_4$ haloalkylcarbonyl; naphthyl; benzoyl; halosubstituted benzoyl; a polycyclic aliphatic group having from 6 to 12 carbon atoms; amino; mono- or di-($C_1$-$C_4$)alkylamino; $C_3$-$C_8$ alkynyl; cyano; benzyl; or a saturated or unsaturated heterocyclic ring containing from 5 to 6 atoms including from 1 to 2 hetero atoms selected from oxygen and sulfur, optionally substituted by from 1 to 3 methyl groups and/or from 1 to 2 oxo groups; and m is 0 or 1;
provided that:
(a) when A is —NH— and $R_2$ is phenyl or substituted phenyl, then W is oxygen; and
(b) when A is oxygen and $R_2$ is substituted phenyl, the substituents on the phenyl ring are not meta-directing electron-withdrawing groups; and
(c) when $R_2$ is cyano or $C_3$-$C_8$ alkynyl and m is 1, then A is —$CH_2$—.

2. A compound according to claim 1 in which Y and Z are hydrogen.

3. A compound according to claim 1 in which X is halo, nitro, perhalomethyl, di- or trifluoromethoxy, difluoromethyl or tetrafluoroethoxy.

4. A compound according to claim 3 in which Y and Z are hydrogen.

5. A compound according to claim 1 in which Y is hydrogen and Z is fluoro.

6. A compound according to claim 1 in which Y is 5-halo or 5-trifluoromethyl.

7. A compound according to claim 1 in which m is 0.

8. A compound according to claim 7 in which $R_2$ is $C_1$-$C_6$ alkyl, $C_2$-$C_6$ alkenyl, $C_2$-$C_4$ haloalkyl, $C_3$-$C_6$ cycloalkyl, $C_1$-$C_6$ carboalkoxy, $C_1$-$C_6$ carboalkoxy-($C_1$-$C_2$)-alkylene, di-$C_1$-$C_4$ alkylamino or a 5- to 6-membered saturated or unsaturated heterocyclic ring containing from 1 to 2 oxygen or sulfur atoms.

9. A compound according to claim 1 in which m is 1 and Z is oxygen, sulfur, $CH_2$ or —NH—.

10. A compound according to claim 9 in which $R_2$ is $C_1$-$C_6$ alkyl, $C_1$-$C_5$ alkoxy, $C_1$-$C_6$ carboalkoxy; $C_1$-$C_6$ carboalkoxy-($C_1$-$C_2$)-alkylene, $C_3$-$C_6$ cycloalkyl, halophenoxy, p-chlorosulfonyl, $C_2$-$C_6$ alkenyl, $C_2$-$C_4$ haloalkylcarbonyl, halosubstituted phenyl or a 5- or 6-membered saturated or unsaturated heterocyclic ring containing 1 or 2 sulfur or oxygen atoms.

11. A compound according to claim 1 in which W is oxygen; X is trifluoromethyl or halo; Y is hydrogen; Z is hydrogen and $R_1$ is ethyl.

12. A compound according to claim 11 in which $R_2$ is $C_1$-$C_6$ alkyl, $C_2$-$C_6$ alkenyl, $C_1$-$C_5$ alkoxy, $C_1$-$C_4$ haloalkyl, if m is 1; $C_2$-$C_4$ haloalkyl is m is 0; $C_3$-$C_6$ cycloalkyl, di-($C_1$-$C_4$ alkyl)amino, halosubstituted phenyl, halo-substituted phenoxy, p-chlorophenylsulfonyl, $C_2$-$C_4$ haloalkylcarbonyl, $C_1$-$C_6$ carboalkoxy, $C_1$-$C_6$ carboalkoxy-($C_1$-$C_2$)alkylene or a 5- to 6-membered saturated or unsaturated heterocyclic ring containing 1 or 2 oxygen or sulfur atoms.

13. A compound according to claim 1 in which X is trifluoromethyl, Y is hydrogen, Z is hydrogen, W is oxygen, m is 0; $R_1$ is ethyl and $R_2$ is isobutyl.

14. A compound according to claim 1 in which X is trifluoromethyl, Y is hydrogen, Z is hydrogen, W is oxygen, m is 1, A is oxygen; $R_1$ is ethyl and $R_2$ is isopropyl.

15. A compound according to claim 1 in which X is trifluoromethyl, Y is hydrogen, Z is hydrogen, W is oxygen, m is 0; $R_1$ is ethyl and $R_2$ is cyclopropyl.

16. A compound according to claim 1 in which X is trifluoromethyl, Y is hydrogen, Z is hydrogen, W is oxygen, m is 1, A is oxygen; $R_1$ is ethyl and $R_2$ is 3-tetrahydrofuryl.

17. A compound according to claim 1 in which X is trifluoromethyl, Y is hydrogen, Z is hydrogen, W is oxygen, m is 0; $R_1$ is ethyl and $R_2$ is secondary butyl.

18. A compound according to claim 1 in which X is trifluoromethyl, Y is hydrogen, Z is hydrogen, W is oxygen, m is 0; $R_1$ is ethyl and $R_2$ is neopentyl.

19. A compound according to claim 1 in which X is trifluoromethyl, Y is hydrogen, Z is hydrogen, W is oxygen, m is 0; $R_1$ is ethyl and $R_2$ is 3,3,3-trifluoro-2-methylpropyl.

20. A compound according to claim 1 in which X is trifluoromethyl, Y is hydrogen, Z is hydrogen, W is oxygen, m is 1, A is —$CH_2$—; $R_1$ is ethyl and $R_2$ is cyclopentyl.

21. A compound according to claim 1 in which X is chloro, Y is hydrogen, Z is fluoro, W is oxygen, m is 1, A is oxygen; $R_1$ is ethyl and $R_2$ is isopropyl.

22. A compound according to claim 1 in which X is cyano, Y is hydrogen, Z is hydrogen, W is oxygen, m is 1, A is oxygen; $R_1$ is ethyl and $R_2$ is isopropyl.

23. A compound according to claim 1 in which X is trifluoromethyl, Y is hydrogen, Z is fluoro, W is oxygen, m is 1, A is oxygen; $R_1$ is ethyl and $R_2$ is isopropyl.

24. A compound according to claim 1 in which X is chloro, Y is hydrogen, Z is hydrogen, W is oxygen, m is 1, A is oxygen; $R_1$ is ethyl and $R_2$ is isopropyl.

25. A compound according to claim 1 in which X is trifluoromethyl, Y is hydrogen, Z is hydrogen, W is oxygen, m is 1, A is —NH—; $R_1$ is ethyl and $R_2$ is ethyl.

26. A compound according to claim 1 in which X is trifluoromethyl, Y is hydrogen, Z is hydrogen, W is oxygen, m is 1, A is —NH—; $R_1$ is ethyl and $R_2$ is tertiary butyl.

27. A compound according to claim 1 in which X is nitro, Y is hydrogen, Z is hydrogen, W is oxygen, m is 1, A is O; $R_1$ is ethyl and $R_2$ is isopropyl.

28. A compound according to claim 1 in which X is trifluoromethyl, Y is hydrogen, Z is hydrogen, W is oxygen, m is 1, A is —$CH_2$—; $R_1$ is ethyl and $R_2$ is 4-fluorophenyl.

29. A compound according to claim 1 in which X is trifluoromethyl, Y is hydrogen, Z is hydrogen, W is oxygen, m is 0; $R_1$ is ethyl and $R_2$ is 1-methylcyclopropyl.

30. A compound according to claim 1 in which X is trifluoromethyl, Y is hydrogen, Z is hydrogen, W is oxygen, m is 0; $R_1$ is ethyl and $R_2$ is trans-2-methylcyclopropyl.

31. A compound according to claim 1 in which X is trifluoromethyl, Y is hydrogen, Z is hydrogen, W is oxygen, m is 1, A is oxygen; $R_1$ is chloromethyl and $R_2$ is isopropyl.

32. A compound according to claim 1 in which X is trifluoromethyl, Y is hydrogen, Z is fluoro, W is oxygen, m is 0; $R_1$ is ethyl and $R_2$ is cyclopropyl.

33. An herbicidal composition containing (a) a herbicidally effective amount of a compound according to claim 1 and (b) a herbicidally suitable inert diluent or carrier.

34. A method of controlling undesirable vegetation comprising applying to said vegetation or the locus thereof a herbicidally effective amount of a compound according to claim 1.

35. A method of controlling undesirable vegetation comprising applying to said vegetation or the locus thereof a herbicidally effective amount of a composition according to claim 33.

* * * * *